US011419489B2

(12) United States Patent
Iwasaki

(10) Patent No.: US 11,419,489 B2
(45) Date of Patent: Aug. 23, 2022

(54) CLEANING TOOL FOR INSERTION INSTRUMENT

(71) Applicant: OLYMPUS CORPORATION, Tokyo (JP)

(72) Inventor: Tomokazu Iwasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 180 days.

(21) Appl. No.: 16/935,747

(22) Filed: Jul. 22, 2020

(65) Prior Publication Data

US 2020/0359882 A1 Nov. 19, 2020

Related U.S. Application Data

(63) Continuation of application No. PCT/JP2018/032169, filed on Aug. 30, 2018.

(30) Foreign Application Priority Data

Jan. 31, 2018 (JP) .............................. JP2018-015054

(51) Int. Cl.
*A61B 1/12* (2006.01)
*B08B 9/032* (2006.01)
(Continued)

(52) U.S. Cl.
CPC .............. *A61B 1/122* (2013.01); *B08B 9/032* (2013.01); *A61B 1/00098* (2013.01);
(Continued)

(58) Field of Classification Search
CPC ..... G02B 23/24; A61B 1/122; A61B 1/00101; A61B 1/125; A61B 1/00098; B08B 9/032
See application file for complete search history.

(56) References Cited

U.S. PATENT DOCUMENTS 5,733,244 A * 3/1998 Yasui .................. A61M 13/003
600/129
5,795,404 A * 8/1998 Murphy ................ B08B 9/0321
134/22.12
(Continued)

FOREIGN PATENT DOCUMENTS

EP 3 207 857 A1 8/2017
JP 58-133230 A 8/1983
(Continued)

OTHER PUBLICATIONS

International Search Report dated Nov. 20, 2018 received in PCT/JP2018/032169.

*Primary Examiner* — Benjamin L Osterhout
(74) *Attorney, Agent, or Firm* — Scully, Scott, Murphy & Presser, P.C.

(57) ABSTRACT

A cleaning tool for insertion instrument includes: a cleaning cap configured to be attachable to and detachable from a distal end component portion provided on a distal end side of an insertion portion in an endoscope and covered by a tubular cover when the endoscope is used, attachment and detachment of the cleaning cap to and from the distal end component portion being performed in a state where the cover is removed from the distal end component portion; and a cap-side engaging portion provided on the cleaning cap and configured to be engaged with a distal end component portion-side engaging portion provided on an outer peripheral surface, at least a part of which is covered by the cover, of the distal end component portion.

13 Claims, 10 Drawing Sheets

(51) Int. Cl.
   *G02B 23/24* (2006.01)
   *A61B 1/00* (2006.01)

(52) U.S. Cl.
   CPC .......... *A61B 1/00101* (2013.01); *A61B 1/125* (2013.01); *G02B 23/24* (2013.01)

(56) References Cited

U.S. PATENT DOCUMENTS

| | | | |
|---|---|---|---|
| 10,307,041 B2* | 6/2019 | Wu | A61B 1/126 |
| 2004/0254421 A1* | 12/2004 | James | A61B 1/2676 |
| | | | 600/127 |
| 2016/0270634 A1* | 9/2016 | Tanaka | A61B 1/00098 |
| 2016/0270637 A1* | 9/2016 | Tanaka | A61B 1/00098 |
| 2017/0181612 A1 | 6/2017 | Yamaya | |
| 2017/0182520 A1* | 6/2017 | Yamaya | B08B 3/02 |
| 2018/0185045 A1* | 7/2018 | Ohki | A61B 1/00098 |
| 2019/0223697 A1* | 7/2019 | Hosogoe | A61B 1/018 |

FOREIGN PATENT DOCUMENTS

| | | |
|---|---|---|
| JP | 4855824 B2 | 1/2012 |
| JP | 2015-181914 A1 | 10/2015 |
| JP | 6368888 B1 | 8/2018 |
| WO | 2015/107801 A1 | 7/2015 |
| WO | 2016/059921 A1 | 4/2016 |
| WO | 2018/037727 A1 | 3/2018 |

* cited by examiner

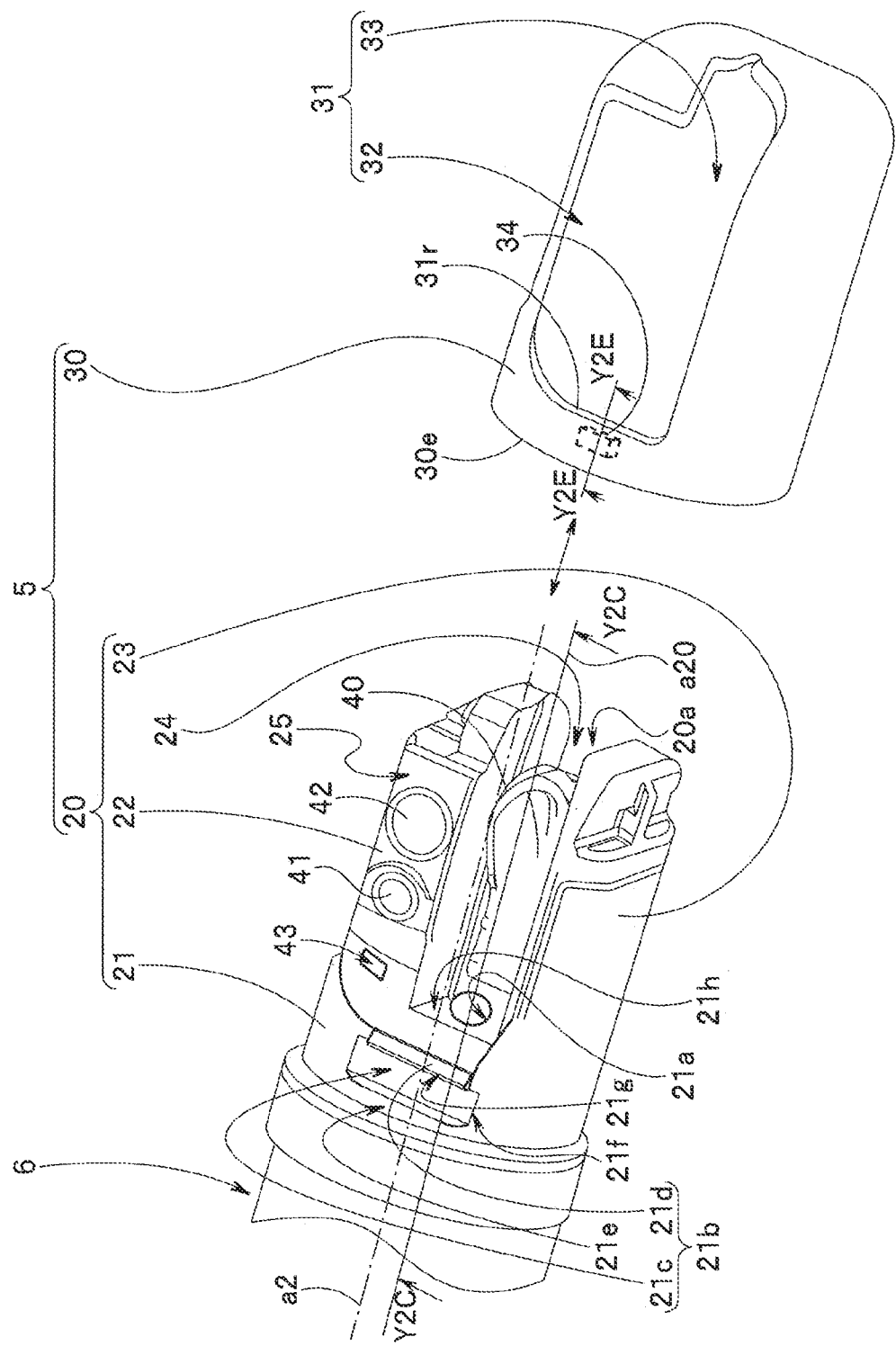

CLEANING TOOL FOR INSERTION INSTRUMENT

CROSS REFERENCE TO RELATED APPLICATION

This application is a continuation application of PCT/JP2018/032169 filed on Aug. 30, 2018 and claims benefit of Japanese Application No. 2018-015054 filed in Japan on Jan. 31, 2018, the entire contents of which are incorporated herein by this reference.

BACKGROUND OF THE INVENTION

1. Field of the Invention

The present invention relates to a cleaning tool for insertion instrument used for cleaning a distal end component portion provided at a distal end portion of an insertion portion of an insertion instrument.

2. Description of the Related Art

An example of an insertion instrument includes a medical endoscope. The endoscope includes an insertion portion, and a distal end component portion is provided on a distal end side of the insertion portion. The endoscope includes a front-view type endoscope in which an illumination lens and an objective lens are arranged on a distal end surface substantially orthogonal to an insertion-portion longitudinal axis of the distal end component portion or a side-view type endoscope in which an illumination lens and an objective lens are arranged on a side surface substantially parallel to the insertion-portion longitudinal axis of the distal end component portion.

The side-view type endoscope is a so-called duodenoscope and the like, and a turnable raising apparatus is provided at the distal end component portion. The distal end component portion including the raising apparatus is covered by a distal end cover having electrical insulation properties. The distal end cover is fixed to the distal end component portion by an adhesive or the like to prevent the distal end cover from falling off the distal end component portion.

The raising apparatus is typically configured mainly by a raising base turnably arranged on the distal end component portion, a raising base operation lever provided on an operation portion, and a raising base operation wire that moves with an operation of the raising base operation lever and swings the raising base.

A treatment instrument channel, into which a treatment instrument is inserted, is provided in the insertion portion of the side-view type endoscope. After being inserted into the treatment instrument channel, the treatment instrument is guided to the vicinity of a target site by passing onto the raising base from a distal end opening provided in the distal end component portion. A position of the distal position of the guided treatment instrument can be changed when the raising base is caused to swing by the operation of the raising base operation lever from a user.

Examples of the treatment instrument inserted into the treatment instrument channel include a contrast tube, a basket catheter, a balloon catheter, and an electric scalpel.

The endoscope is cleaned and disinfected after being used.

Japanese Patent Application Laid-Open Publication No. 2015-181914 discloses an endoscope cleaning attachment in which cleaning and disinfection work can be quickly performed by reliably supplying a cleaning liquid or the like to a target site in an accommodation chamber of a distal end component portion for endoscope where a treatment instrument raising base is turnably disposed.

Japanese Patent No. 4855824 discloses a distal end cover for endoscope capable of being removed from a distal end component portion by tearing and breaking the distal end cover for endoscope without damaging a soft member that configures an insertion portion, and capable of being prevented from falling off at the time of use.

When the insertion portion of the side-view type endoscope is cleaned, the cleaning can be easily performed by removing the distal end cover and exposing the distal end component portion.

SUMMARY OF THE INVENTION

According to an aspect of the present invention, a cleaning tool for insertion instrument includes: a cleaning cap configured to be attachable to and detachable from a distal end component portion provided on a distal end side of an insertion portion in an insertion instrument and covered by a tubular cover when the insertion instrument is used, attachment and detachment of the cleaning cap to and from the distal end component portion being performed in a state where the cover is removed from the distal end component portion; and a cap-side engaging portion provided on the cleaning cap and configured to be engaged with a distal end component portion-side engaging portion provided on an outer peripheral surface, at least a part of which is covered by the cover, of the distal end component portion.

BRIEF DESCRIPTION OF THE DRAWINGS

FIG. 2B is a view illustrating a distal end cover and a distal end component portion being in an exposed state;

DETAILED DESCRIPTION OF THE PREFERRED EMBODIMENT

Figure 1:
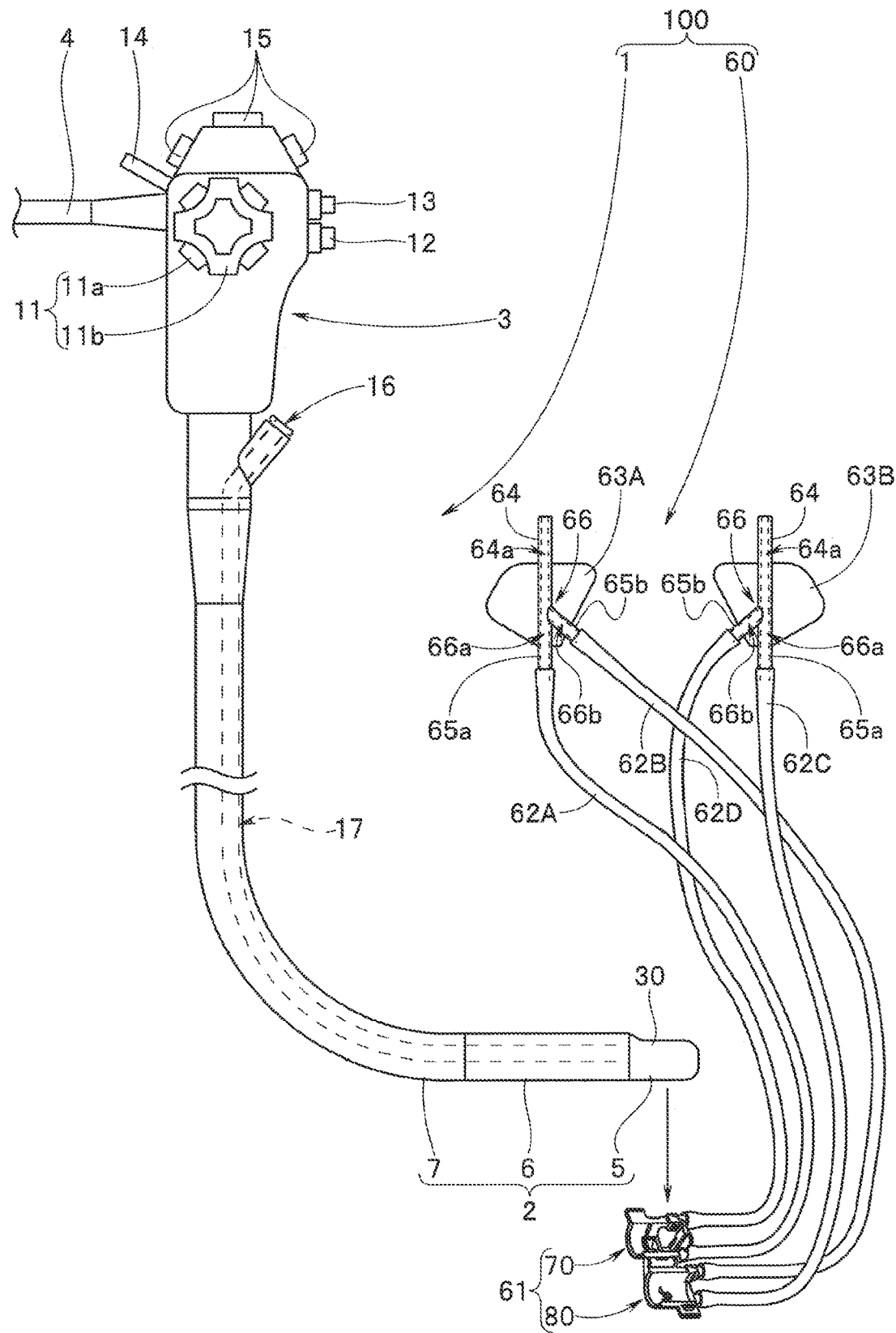
FIG. 1 is a view illustrating an endoscope system including a side-view type endoscope and a cleaning tool for endoscope.

An embodiment of the present invention will be described below with reference to the drawings.

Note that, in each of the drawings used in the following description, scales are varied for some components to show the respective components in recognizable sizes in the drawings. The present invention is not limited only to numbers of the components, shapes of the components, ratios of sizes of the components, and relative positional relations among the respective components shown in the drawings.

In the present embodiment, an insertion instrument shown in FIG. 1 is a side-view type endoscope (hereinafter, abbreviated as an endoscope) 1. Reference numeral 30 refers to a distal end cover (hereinafter, abbreviated as a cover). Reference numeral 60 refers to a cleaning tool for insertion instrument. The cleaning tool for insertion instrument 60 in the present embodiment is a cleaning tool for endoscope.

Therefore, reference numeral 100 in FIG. 1 refers to an endoscope system, and includes the endoscope 1 and the cleaning tool for endoscope 60.

The endoscope 1 shown in FIG. 1 includes an insertion portion 2, an operation portion 3, and a universal cord 4. The insertion portion 2 includes a distal end portion 5, a bending portion 6, and a flexible tube portion 7 which are provided in this order from a distal end side. The bending portion 6 is configured to bend in four direction of up, down, left, and right directions, for example. The insertion portion 2 is inserted into a subject.

The operation portion 3 is provided on a proximal end side of the insertion portion 2. The universal cord 4 extends from a side part of the operation portion 3. The operation portion 3 is provided with a bending operation device 11, an air/water feeding button 12, a suction button 13, a raising base operation lever 14, and various operation switches 15.

Examples of various operation switches 15 include a freeze switch configured to generate a freeze signal, a release switch configured to generate a release signal at the time of photographing, and an observation mode changeover switch configured to give a command to change over an observation mode.

Reference numeral 16 refers to a treatment instrument insertion opening into which a treatment instrument (not shown) is inserted. One end side of a treatment instrument channel tube 17 is connected to the treatment instrument insertion opening 16. The other end side of the treatment instrument channel tube 17 is connected to a distal end component portion (see reference numeral 20 in FIG. 2A, for example) that configures the distal end portion 5 of the insertion portion 2.

When an up/down bending knob 11a of the bending operation device 11 provided in the operation portion 3 is operated to turn, the bending portion 6 bends in an up direction or a down direction. On the other hand, when a left/right bending knob 11b is operated to turn, the bending portion 6 bends in a left direction or a right direction.

Figure 2A:
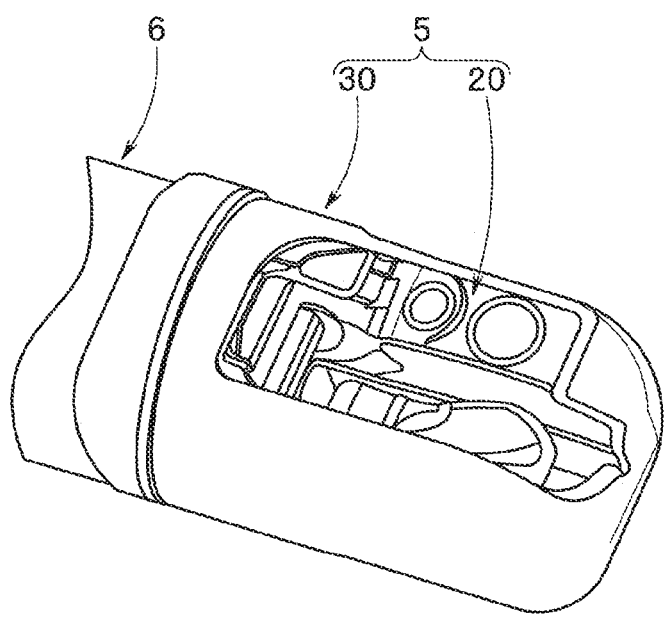
FIG. 2A is a view illustrating a distal end portion in which a distal end component portion located on a distal end side of an insertion portion of an endoscope is covered by a distal end cover.

The distal end portion 5 shown in FIG. 1 is configured in which the distal end component portion 20 is covered by the cover 30 at the time of use of the endoscope as shown in FIG. 2A. The distal end component portion 20 is formed of a rigid member. The cover 30 is formed in a tubular shape and has predetermined resilience. In addition, the cover 30 is made of, for example, a resin having electrical insulation properties.

A configuration of the distal end component portion 20 and the cover 30 and a relation between the two members will be described with reference to FIGS. 2A to 2F.

As shown in FIG. 2B, the distal end component portion 20 includes a distal-end-portion body 21, an optical protrusion portion 22, and a protrusion portion for raising base 23. The distal-end-portion body 21 configures a proximal end portion of the distal end component portion 20, that is, a part closer to the bending portion 6. The distal-end-portion body 21 is provided with a channel opening 21a, which is one opening of a treatment instrument channel 21k, and a body engaging portion 21b.

The body engaging portion 21b is an engaging portion in a distal end component portion side. The body engaging portion 21b is provided at a predetermined position on an outer peripheral surface of the distal-end-portion body 21. The channel opening 21a is provided in a body distal end surface 21h of the distal-end-portion body 21. The body distal end surface 21h is a flat surface orthogonal to a component-portion longitudinal axis a20 of the distal end component portion 20 parallel to an insertion-portion axis a2. In FIG. 2B, the component-portion longitudinal axis a20 passes through a center point (not shown) of the channel opening 21a.

The optical protrusion portion 22 and the protrusion portion for raising base 23 protrude from the body distal end surface 21h in a distal end direction along the component-portion longitudinal axis a20. The optical protrusion portion 22 and the protrusion portion for raising base 23 are provided in parallel. A groove having a predetermined width is provided between the optical protrusion portion 22 and the protrusion portion for raising base 23.

The groove is a raising base accommodating space 24 provided in the distal end component portion 20. A raising base 40 is turnably provided in the raising base accommodating space 24. In the present embodiment, the distal end side of the raising base accommodating space 24 has a function as a distal-end-side engaging portion 20a provided on the distal end side of the distal end component portion 20.

An upper flat surface 25 orthogonal to the body distal end surface 21h is formed on the optical protrusion portion 22. An observation lens 41 and an illumination lens 42 are provided at predetermined positions on the upper flat surface 25. Reference numeral 43 refers to a cleaning nozzle.

Figure 2C:
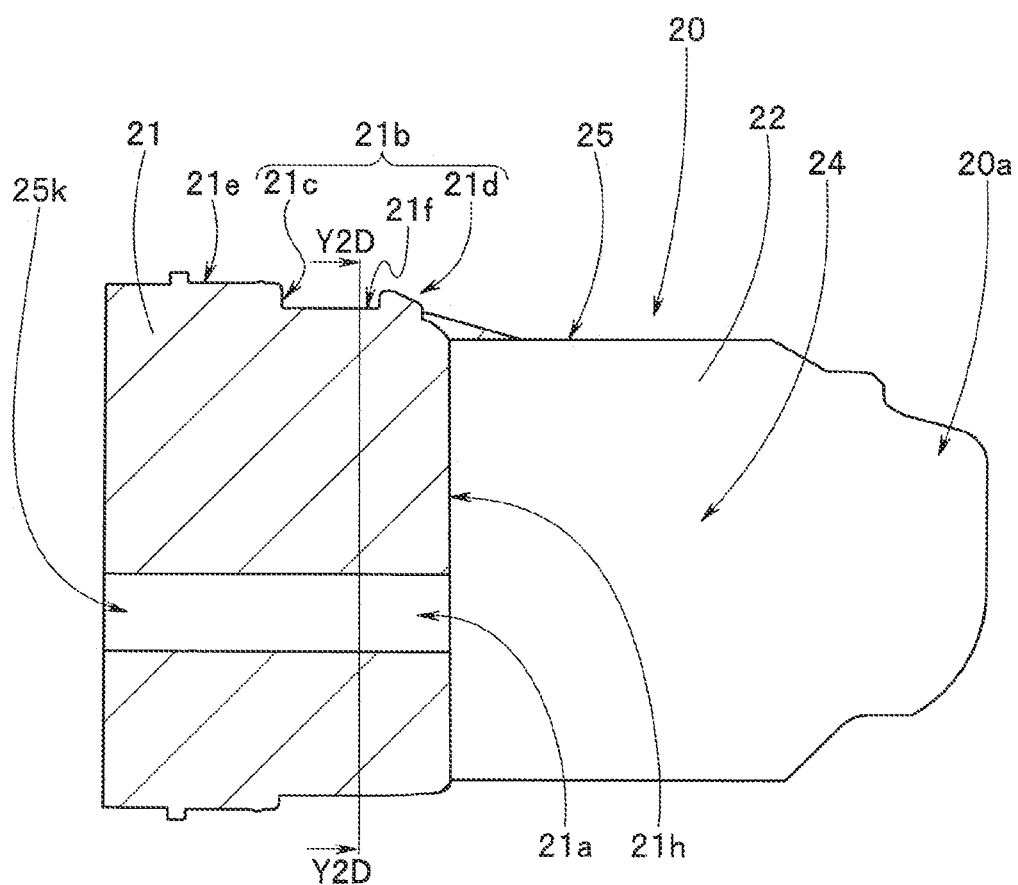
FIG. 2C is a cross-sectional view taken along a line Y2C-Y2C in FIG. 2B.

As shown in FIGS. 2B and 2C, the body engaging portion 21b includes a recess portion 21c and a protrusion portion 21d. The recess portion 21c has a groove shape, and is recessed by a predetermined amount with respect to an arc-shaped upper outer peripheral surface 21e of the distal-end-portion body 21. The protrusion portion 21d protrudes by a predetermined amount with respect to a bottom surface 21f that is a flat surface of the recess portion 21c. The recess portion 21c may not be provided.

The recess portion 21c and the protrusion portion 21d are provided at predetermined position on the distal-end-portion body 21. The protrusion portion 21d is located closer to the raising base accommodating space 24.

Figure 2D:
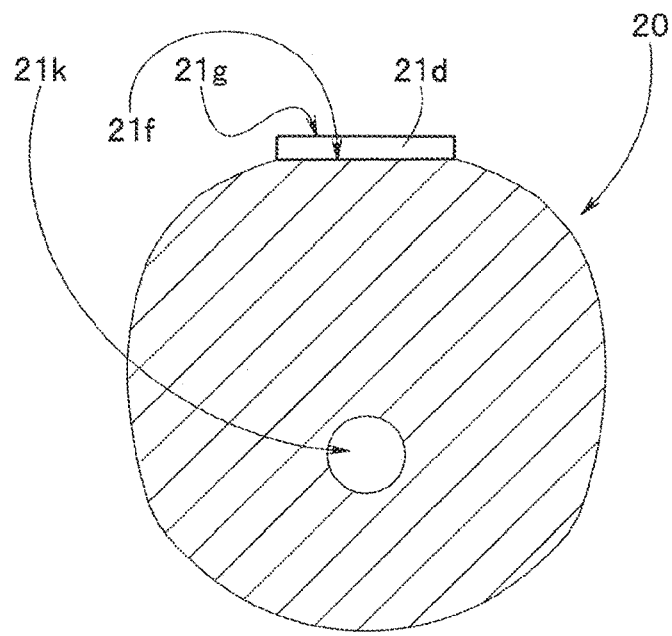
FIG. 2D is a cross-sectional view taken along a line Y2D-Y2D in FIG. 2C.

As shown in FIGS. 2C and 2D, an upper surface 21g, which is one surface of the protrusion portion 21d, is formed parallel to a tangent line of the outer peripheral surface 21e. The bottom surface 21f of the protrusion portion 21d is formed to coincide with the outer peripheral surface 21e.

The body distal end surface 21h is a distal end surface of the distal-end-portion body 21, and is also a bottom surface of the groove that can be the raising base accommodating space 24. The channel opening 21a is one opening of the treatment instrument channel 21k provided in the distal-end-portion body 21.

The other end side of the treatment instrument channel tube 17 described above is connected to the other opening of the treatment instrument channel 21k. Therefore, the treatment instrument inserted from the treatment instrument insertion opening 16 passes through the treatment instrument channel tube 17 and the treatment instrument channel 21k and is led out from the channel opening 21a to the raising base accommodating space 24.

The cover 30 will be described below.

As described above, the cover 30 has the tubular shape and covers the distal end component portion 20. As shown in FIG. 2B, the cover 30 includes one opening 31 provided at a predetermined position, for example, the upper surface, to penetrate through the inside and the outside of the cover 30. The opening 31 includes an optical opening portion 32 and an opening portion for raising base 33.

The optical opening portion 32 causes the illumination lens 42 and the observation lens 41, which are provided on the upper flat surface 25 of the distal end component portion 20, to be exposed. The opening portion for raising base 33 causes the raising base accommodating space 24 to be exposed. A part of the optical opening portion 32 and a part of the opening portion for raising base 33 join to each other to form one opening 31. Reference numeral 34 refers to a cover-side engaging portion.

Figure 2E:
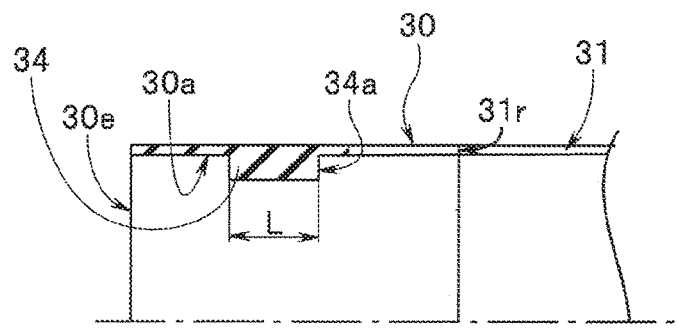
FIG. 2E is a cross-sectional view taken along a line Y2E-Y2E in FIG. 2B.

As shown in FIG. 2E, the cover-side engaging portion 34 is a protrusion portion that protrudes by a predetermined amount from a tubular inner side surface 30a of the cover 30. The cover-side engaging portion 34 is provided at a position spaced from the opening-proximal end surface 31r forming the opening 31 on a cover-proximal end 30e side. Specifically, the cover-side engaging portion 34 includes a cover contact surface 34a at a position spaced by a predetermined distance from the opening-proximal end surface 31r of the opening 31. A length L in a cover-axial direction of the cover-side engaging portion 34 is set to a predetermined length.

A state in which the cover 30 covers the distal end component portion 20 will be described below.

Figure 2F:
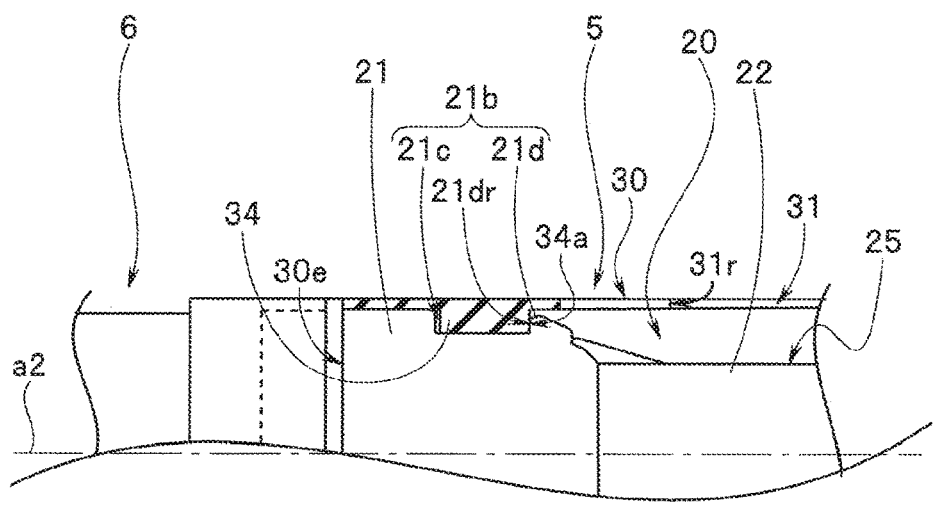
FIG. 2F is a view illustrating a state where a cover-side engaging portion of a cover is engaged with a body engaging portion of a distal end component portion.

The cover 30 covers the distal end component portion 20. At this time, the cover 30 is elastically deformed such that the cover-side engaging portion 34 is arranged in the recess portion 21c of the body engaging portion 21b of the distal end component portion 20 as shown in FIG. 2F.

In such an arrangement, when the cover 30 moves to a distal end side of the insertion-portion longitudinal axis a2, the cover contact surface 34a of the cover-side engaging portion 34 disposed in the recess portion 21c comes in contact with a proximal end surface 21dr of the protrusion portion 21d. As a result, the movement of the cover 30 toward the distal end of the insertion-portion longitudinal axis a2 is prevented. Accordingly, the cover 30 is prevented from falling off the distal end component portion 20.

In such a structure, even when the cover-side engaging portion 34 is not provided and the opening-proximal end surface 31r rather than the cover contact surface 34a comes in contact with the proximal end surface 21dr of the protrusion portion 21d, the same operational effect can be obtained. In this case, the protrusion portion 21d is exposed frontward from the opening-proximal end surface 31r.

In addition, the upper surface 21g of the protrusion portion 21d is formed to be parallel to the tangent line of the outer peripheral surface 21e as shown in FIG. 2D, so that the distal end cover 30 is strongly caught at both ends of the protrusion portion 21d. Thus, the distal end cover 30 is further reliably prevented from moving toward the distal end of the insertion-portion longitudinal axis a2 and from falling off the distal end component portion 20.

A configuration of the cleaning tool for endoscope 60 and a relation between the cleaning tool for endoscope 60 and the distal end component portion 20 will be described with reference to FIGS. 3A to 3E.

As shown in FIG. 1, the cleaning tool for endoscope 60 of the present embodiment mainly includes a cleaning cap 61, four tube bodies 62, and two injection portions 63.

The cleaning cap 61 is divided into a first cap portion 70 and a second cap portion 80. The four tube bodies 62 are described as a first tube 62A, a second tube 62B, a third tube 62C, and a fourth tube 62D, respectively, to distinguish from each other. In addition, the two injection portions 63 are described as a first injection portion 63A and a second injection portion 63B, respectively, to distinguish from each other.

Each of the injection portions 63A and 63B includes one connection port 64 and two supply ports 65a and 65b. For example, a syringe (not shown) filled with a cleaning liquid is connected to the connection ports 64 of the injection portions 63A and 63B.

One end portions of the tubes 62A and 62B are coupled to the first supply port 65a and the second supply port 65b of the first injection portion 63A, respectively. On the other hand, one end portions of the tubes 62C and 62D are coupled to the first supply port 65a and the second supply port 65b of the second injection portion 63B, respectively.

The other end portions of the tubes 62A, 62B, 62C, and 62D are connected to the cap portions 70 and 80, respectively, as will be described below.

Reference numeral 66 refers to a branching portion. An injection path 64a provided in the connection port 64 is branched at the branching portion 66 into a first supply path 66a directed to the first supply port 65a and a second supply path 66b directed to the second supply port 65b.

As shown in FIGS. 3A to 3D, the first cap portion 70 and the second cap portion 80 of the cleaning cap 61 divided into two portions are coupled to each other so as to be turnable around a shaft portion 91 of a hinge structure portion 90.

Reference numeral 79 refers to an engagement step portion provided on the first cap portion 70. Reference numeral 89 refers to a claw portion provided on the second cap portion 80. The first cap portion 70 and the second cap portion 80 changes from an open state shown in FIG. 3B to a closed state of a first division surface 70a of the first cap portion 70 and a second division surface 80a of the second cap portion 80. In the closed state as shown in FIG. 3D, the claw portion 89 is engaged with the engagement step portion 79 and the first cap portion 70 and the second cap portion 80 are integrally held.

Figure 3A:
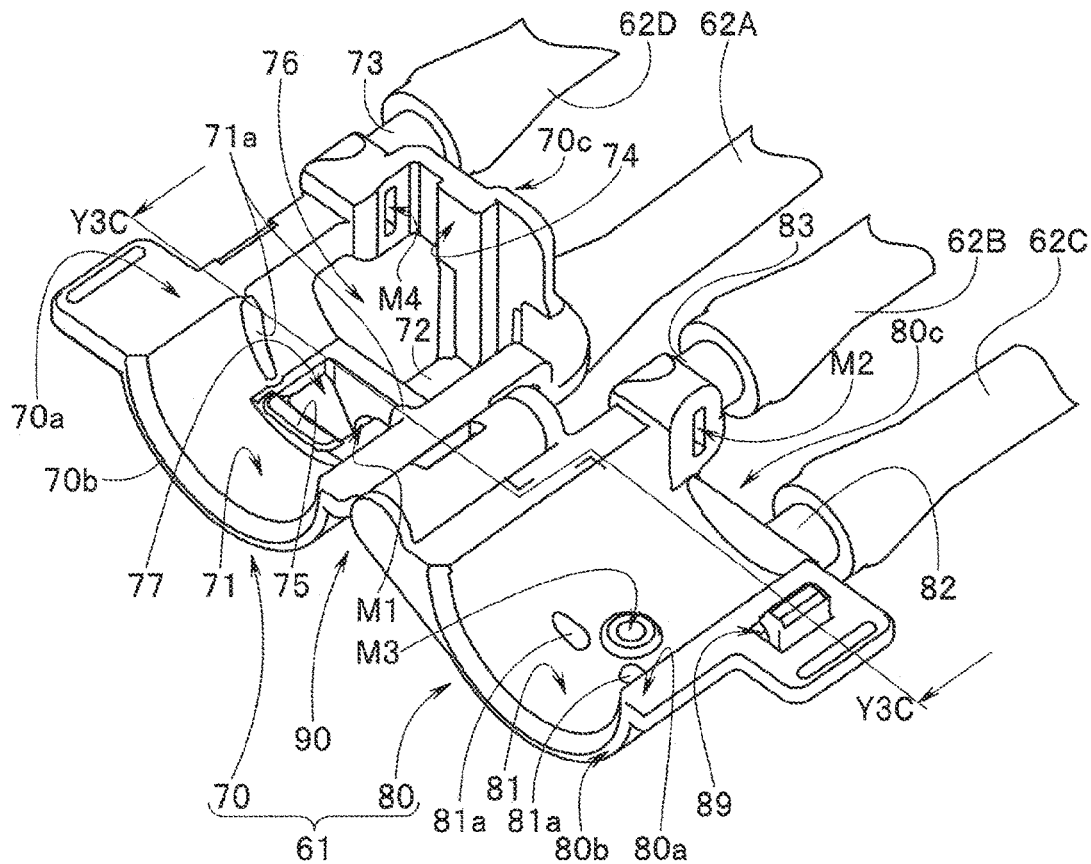
FIG. 3A is a perspective view illustrating a cleaning cap.
Figure 3B:
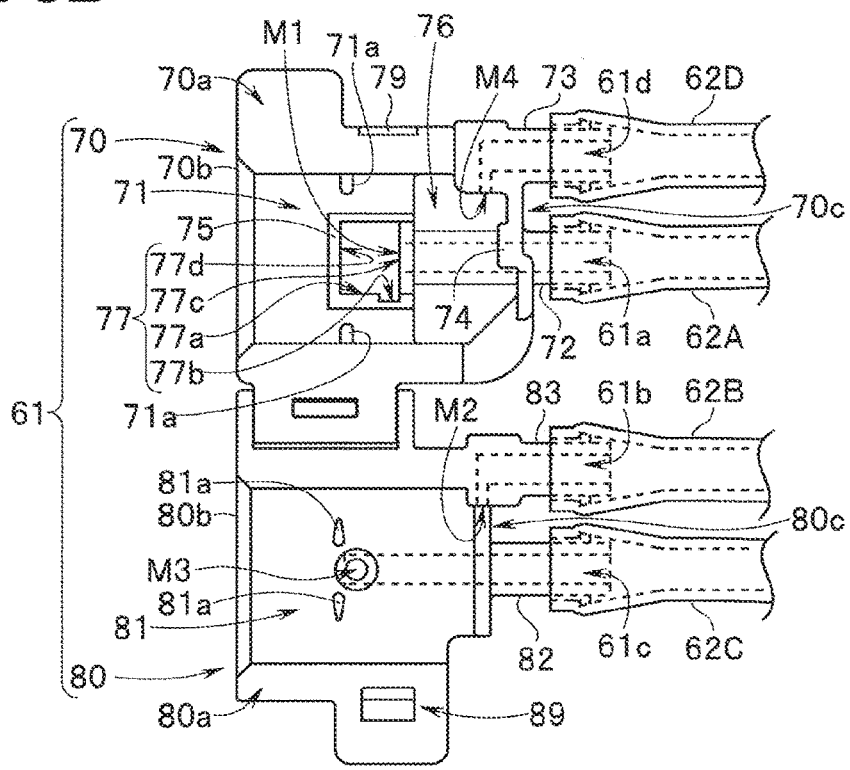
FIG. 3B is a view illustrating the cleaning cap when viewed at a divided surface.

As shown in FIGS. 3A and 3B, the first cap portion 70 mainly includes a first accommodation recess portion for distal end component portion (hereinafter, abbreviated as a first recess portion) 71, a first pipe conduit for first cap 72, a second pipe conduit for first cap 73, a cap bottom engaging portion 74, a cap-side engaging portion 75, a discharge opening 76, and a jetting hole 77. On the other hand, the second cap portion 80 mainly includes a second accommodation recess portion for distal end component portion (hereinafter, abbreviated as a second recess portion) 81, a first pipe conduit for second cap 82, and a second pipe conduit for second cap 83.

The first pipe conduit for second cap 82 includes a second cleaning path 61*b*, and is coupled to the other end portion of the second tube 62B. The second pipe conduit for second cap 83 includes a third cleaning path 61*c*, and is coupled to the other end portion of the third tube 62C. On the other hand, the first pipe conduit for first cap 72 includes a first cleaning path 61*a*, and is coupled to the other end portion of the first tube 62A. The second pipe conduit for first cap 73 includes a fourth cleaning path 61*d*, and is coupled to the other end portion of the fourth tube 62D.

Then, the cleaning liquid supplied from the injection path 64*a* of the first injection portion 63A passes through the first supply path 66*a* branched in the branching portion 66, the first tube 62A, and the first cleaning path 61*a* to be ejected from a first ejection port M1. Further, the cleaning liquid passes through the second supply path 66*b* branched in the branching portion 66, the second tube 62B, and the second cleaning path 61*b* to be ejected from a second ejection port M2.

On the other hand, the cleaning liquid supplied from the injection path 64*a* of the second injection portion 63B passes through the first supply path 66*a* branched in the branching portion 66, the third tube 62C, and the third cleaning path 61*c* to be ejected from a third ejection port M3. Further, the cleaning liquid passes through the second supply path 66*b* branched in the branching portion 66, the fourth tube 62D, and the fourth cleaning path 61*d* to be ejected from a fourth ejection port M4.

Figure 3C:
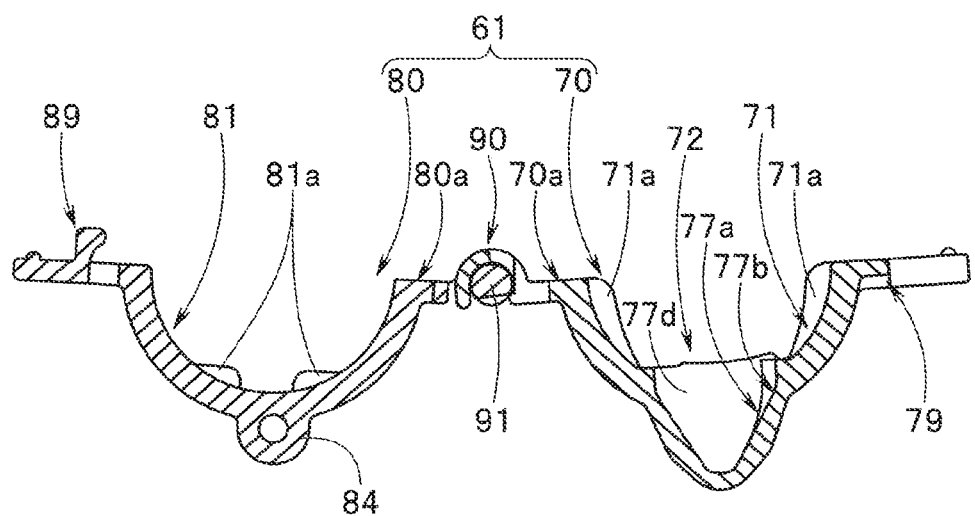
FIG. 3C is a cross-sectional view taken along a line Y3C-Y3C in FIG. 3A.
Figure 3D:
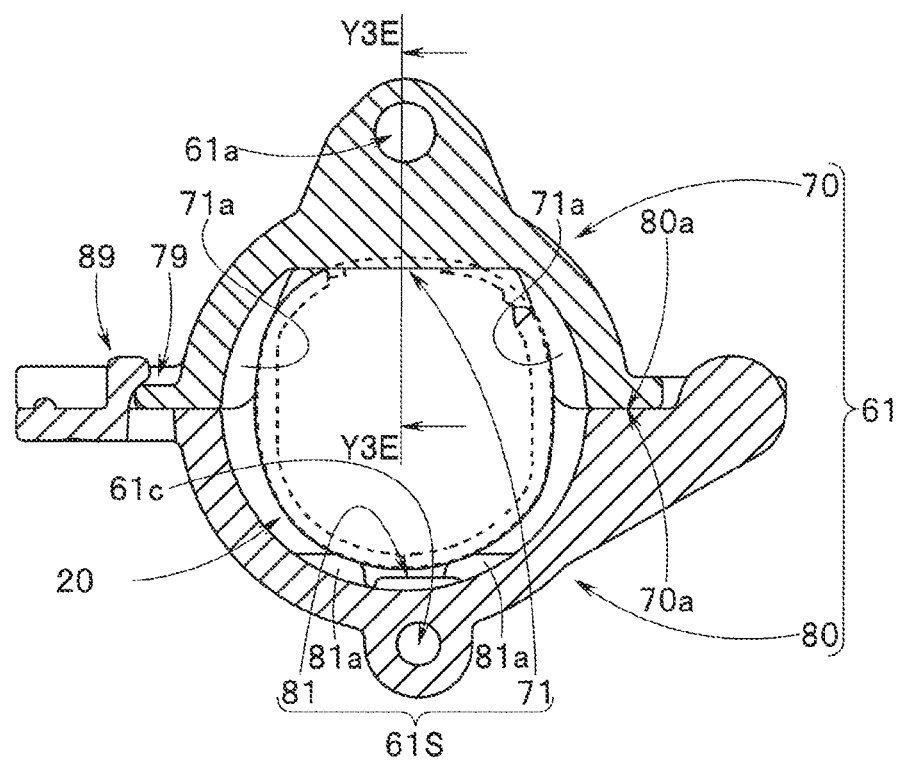
FIG. 3D is a view illustrating a state where divided surfaces of a cap portion are combined.

As shown in FIG. 3C, the first recess portion 71 and the second recess portion 81 are spaces having substantially an arc-shaped cross section. As shown in FIG. 3D, the first division surface 70*a* of the first cap portion 70 is combined with the second division surface 80*a* of the second cap portion 80, thereby a tubular accommodation space 61S is configured to accommodate the distal end component portion 20.

Reference numeral 71*a* refers to a holding projection. A pair of holding projections 71*a* are provided at predetermined positions of the first recess portion 71 so as to face each other. The holding projections 71*a* have a function of holding a predetermined part of the distal end component portion 20 in a substantially linear contact state and a function of preventing the distal end component portion 20 mounted with the cover 30 from being accommodated in the first recess portion 71. In other words, inner diameters of the pair of holding projections 71*a* are set to be larger than the outer diameter of the distal end component portion 20 by a predetermined amount and smaller than the outer diameter of the cover 30 by a predetermined amount.

As shown in FIGS. 3A and 3B, the third ejection port M3 is provided at the center of the bottom surface of the second recess portion 81. The cleaning liquid ejected from the third ejection port M3 is ejected toward the opening of the second recess portion 81. On the other hand, the second ejection port M2 is provided at a cap end portion 80*c* of the second cap portion 80. The cleaning liquid ejected from the second ejection port M2 is ejected in a direction toward the second division surface 80*a* located on the opposite side across the second recess portion 81.

Reference numeral 81*a* refers to a holding projection. A pair of holding projections 81*a* are provided so as to sandwich the third ejection port M3 of the second recess portion 81. The holding projections 81*a* have the configurations and functions similar to the functions of the holding projection 71*a* described above.

On the other hand, on the inner surface of the first recess portion 71, the cap bottom engaging portion 74, the jetting hole 77 located at the center of the bottom surface, and the discharge opening 76 are provided in order from a first-cap proximal end surface 70*b*. On the other hand, the cap bottom engaging portion 74 and the fourth ejection port M4 are provided in a cap end portion 70*c* of the first cap portion 70.

The cap bottom engaging portion 74 is a protrusion portion protruding from an inner surface of an end portion parallel to the first-cap proximal end surface 70*b* of the cap end portion 70*c* toward the first-cap proximal end surface 70*b* by a predetermined amount. The cap bottom engaging portion 74 is formed to engage with the distal-end-side engaging portion 20*a* located on the distal end side of the raising base accommodating space 24.

The fourth ejection port M4 is provided on the side of the first division surface 70*a* at a position on an inner side of the cap end portion 70*c*. The cleaning liquid ejected from the fourth ejection port M4 is ejected in a direction toward the first division surface 70*a* located on the opposite side across the first recess portion 71.

Figure 3E:
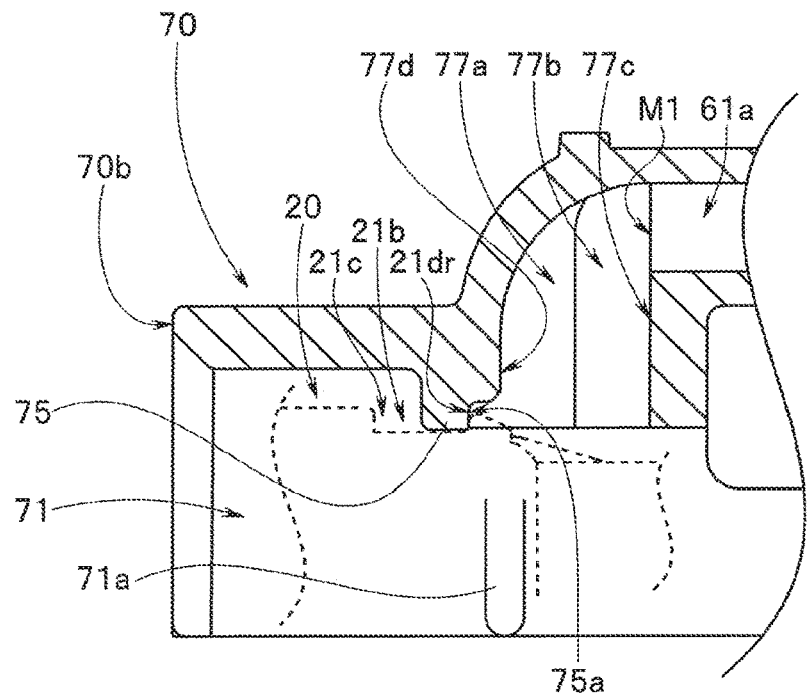
FIG. 3E is a cross-sectional view taken along a line Y3E-Y3E in FIG. 3D and is a view illustrating a cap-side engaging portion.

As shown in FIGS. 3B, 3C, and 3E, the jetting hole 77 includes a first inner peripheral surface 77*a* that guides the cleaning liquid to a hole opening, a second inner peripheral surface 77*b*, a distal end sidewall surface 77*c*, and a proximal end sidewall surface 77*d*.

On the side of the proximal end sidewall surface 77*d*, a cap contact surface (see reference numeral 75*a* in FIG. 3E), which will be described below, is provided to come in contact with the protrusion portion 21*d* configuring the body engaging portion 21*b* of the distal end component portion 20.

The first ejection port M1 is provided on the distal end sidewall surface 77*c*. The first inner peripheral surface 77*a* and the second inner peripheral surface 77*b* are substantially semicircular curved surfaces. The first inner peripheral surface 77*a* and the second inner peripheral surface 77*b* have partially different curvatures for the purpose of changing the ejection direction.

The cleaning liquid ejected from the first ejection port M1 collides with the proximal end sidewall surface 77*d* and is temporarily stored in the jetting hole 77. Then, the cleaning liquid stored in the hole is ejected from the hole opening toward the opening of the first recess portion 71 along the first inner peripheral surface 77*a* and the second inner peripheral surface 77*b*.

Specifically, the cleaning liquid ejected from the hole opening along the first inner peripheral surface 77*a* is directed to the raising base accommodating space 24 of the distal end component portion 20. On the other hand, the cleaning liquid ejected from the hole opening along the second inner peripheral surface 77*b* is directed to the upper flat surface 25 of the distal end component portion 20.

The discharge opening 76 is an opening configured to discharge the cleaning liquid ejected from the ejection ports M1 and M4 or the ejection ports M2 and M3 into the accommodation space 61S to the outside.

As shown in FIG. 3E, the cap-side engaging portion 75 is a protrusion portion provided in the first recess portion 71 of the first cap portion 70 and protruding by a predetermined amount. Reference numeral 75*a* refers to a cap contact surface. The cap contact surface 75*a* is provided at a position spaced from the proximal end sidewall surface 77*d* forming the jetting hole 77 on the first-cap proximal end surface 70*b* side.

The cap-side engaging portion 75 is formed so as to be disposed in the recess portion 21c configuring the body engaging portion 21b of the distal end component portion 20 indicated by a broken line. The cap contact surface 75a of the cap-side engaging portion 75 comes in contact with the proximal end surface 21dr of the protrusion portion 21d, thereby the cleaning cap 61 is prevented from moving toward the distal end side of the distal end component portion 20 and falling off from the distal end component portion 20.

In other words, the cap-side engaging portion 75 and the cover-side engaging portion 34 are disposed in the recess portion 21c of the body engaging portion 21b of the distal end component portion 20, and is also formed in the same shape so as to come in contact with the proximal end surface 21dr.

A relation between the cleaning cap 61 and the distal end component portion 20 configured as described above will be described with reference to FIGS. 4A to 4D.

When the endoscope 1 is cleaned after being used, an operator removes the cover 30 from the distal end component portion 20 configuring the distal end portion 5 of the insertion portion 2 in advance. Then, the operator attaches the cleaning cap 61 to the exposed distal end component portion 20.

Figure 4A:
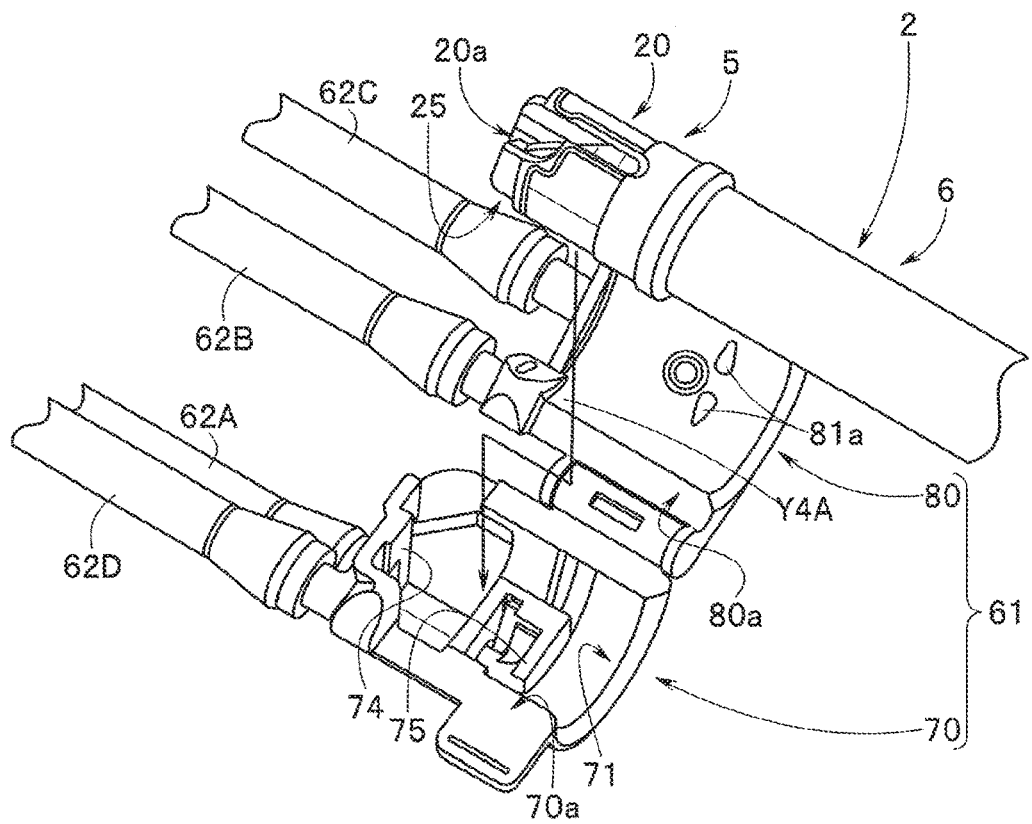
FIG. 4A is a view illustrating a distal end component portion and a distal end cap that are exposed on the distal end side of the insertion portion.

Here, as shown in FIG. 4A, the operator causes the upper surface of the distal end component portion 20 exposed onto the distal end side of the insertion portion 2 to approach the first recess portion 71 as indicated by an arrow Y4A in a state where the upper surface faces the inner surface of the first recess portion 71 of the first cap portion 70 configuring the cleaning cap 61.

At this time, the operator moves the cap-side engaging portion 75 toward the recess portion 21c of the body engaging portion 21b as shown in FIG. 3E or the like while guiding the cap bottom engaging portion 74 of the first cap portion 70 into the distal-end-side engaging portion 20a located on the distal end side of the distal end component portion 20.

Figure 4B:
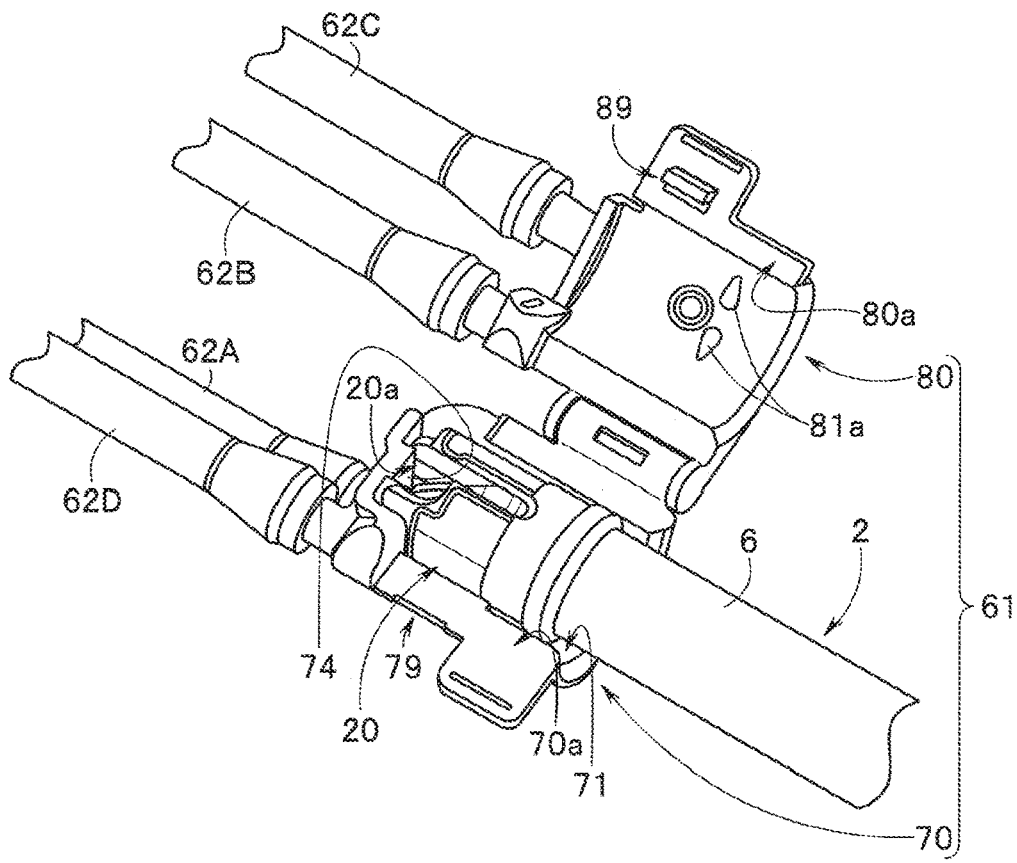
FIG. 4B is a view illustrating a state where the distal end component portion is disposed in a first cap portion of the distal end cap.

Then, as shown in FIG. 4B, the upper surface of the distal end component portion 20 is disposed in the first recess portion 71 of the first cap portion 70 of the cleaning cap 61. At this time, the cap bottom engaging portion 74 of the first cap portion 70 is disposed in the distal-end-side engaging portion 20a. In addition, as shown in FIG. 3E, the cap-side engaging portion 75 is disposed in the recess portion 21c of the body engaging portion 21b.

Figure 4C:
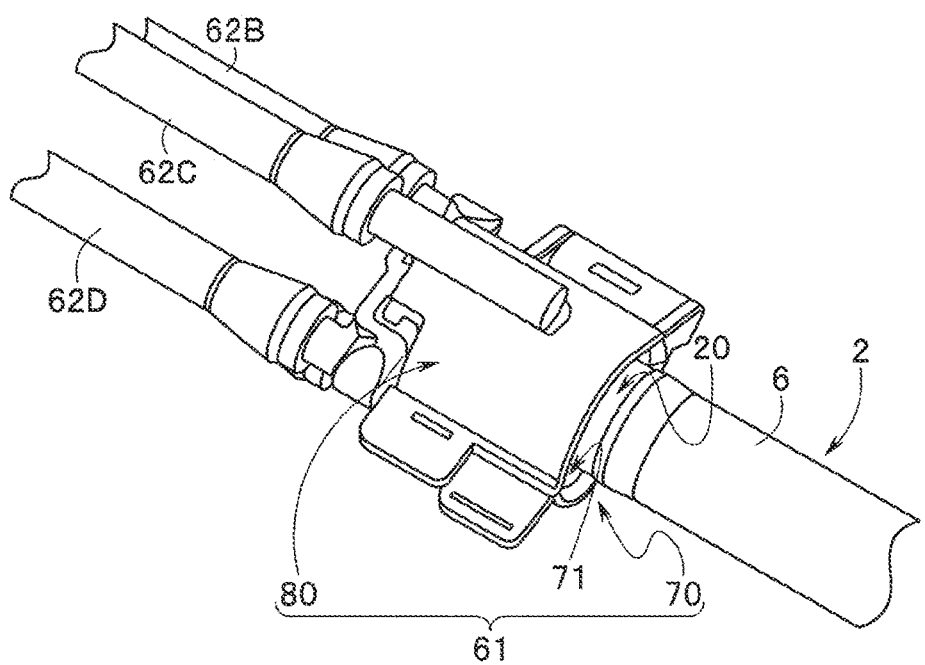
FIG. 4C is a view illustrating a state where the distal end cap is mounted on the distal end component portion.

Here, the operator closes the second cap portion 80, which is in the open state, as shown in FIG. 4B. At this time, the claw portion 89 is engaged with the engagement step portion 79. As a result, as shown in FIG. 4C, the first cap portion 70 and the second cap portion 80 are integrally held, and the mounting of the cleaning cap 61 on the distal end component portion 20 is completed.

Figure 4D:
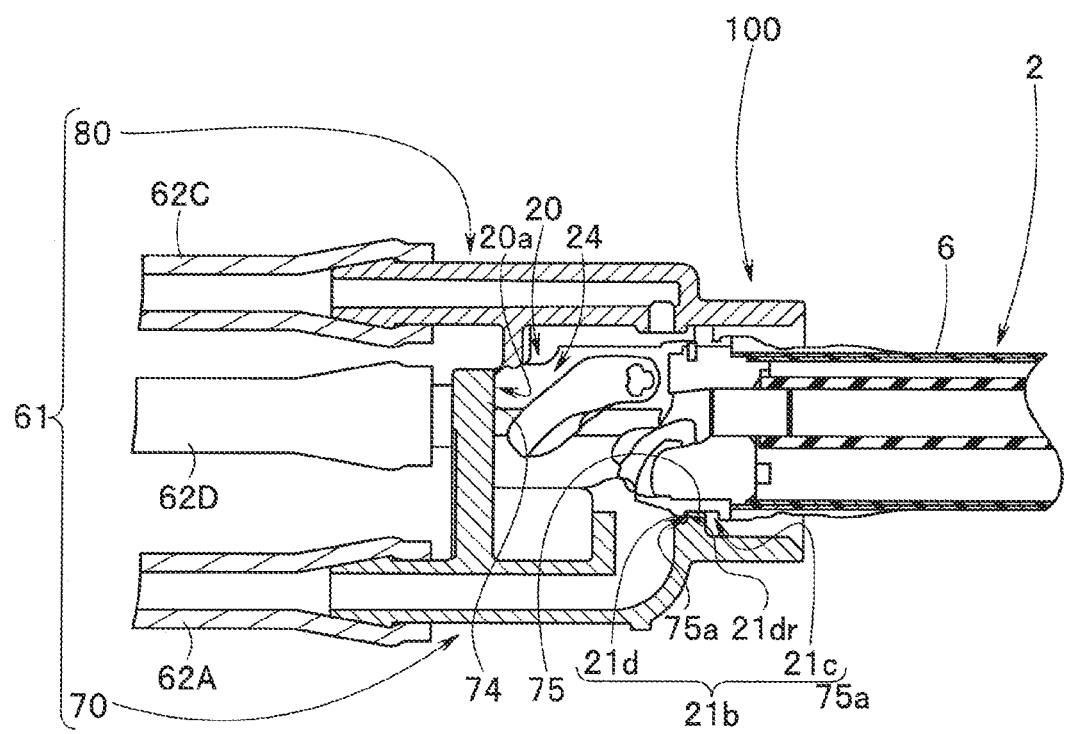
FIG. 4D is a view illustrating a state where the distal end cap in a mounted state is engaged with the distal end component portion.

In such a mounted state, as shown in FIG. 4D, the cap bottom engaging portion 74 is disposed in the distal-end-side engaging portion 20a. Thus, the cleaning cap 61 can be restricted from turning around the insertion-portion longitudinal axis a2. In addition, the cap-side engaging portion 75 is disposed in the recess portion 21c of the body engaging portion 21b.

Therefore, when the cleaning cap 61 moves in the distal end direction of the insertion-portion longitudinal axis a2, the cap contact surface 75a of the cap-side engaging portion 75 comes in contact with the proximal end surface 21dr of the protrusion portion 21d, thereby the cleaning cap 61 can be prevented from falling off the distal end component portion 20.

As described above, the body engaging portion 21b is provided in the distal end component portion 20 and the cover-side engaging portion 34 is provided in the cover 30 such that the cover 30 is prevented from moving in the direction of the insertion-portion longitudinal axis a2 of the insertion portion 2 and the cover 30 is prevented from falling off the distal end side of the distal end component portion 20.

When cleaning the distal end component portion 20, the operator removes the cover 30 from the distal end component portion 20, and mounts the cleaning cap 61 including four ejection ports, which are configured to eject the cleaning liquid, to the distal end component portion 20 exposed by the removal of the cover 30, and cleans the distal end component portion 20.

Since the cleaning cap 61 is divided into the first cap portion 70 and the second cap portion 80, the cleaning cap 61 can be easily attached to the distal end component portion 20.

In addition, the first cap portion 70, which is one of the two divided cap portions of the cleaning cap 61, is provided with the cap-side engaging portion 75 serving as a first cap-side engaging portion substantially similar to the cover-side engaging portion 34 of the cover 30 that engages with the body engaging portion 21b.

In addition, the cap bottom engaging portion 74 serving as a second cap-side engaging portion is provided in the first cap portion 70, which is a tubular bottom portion corresponding to the bottom portion of the tubular accommodation space 61S covering the distal end component portion 20 by the combination of the two cap portions 70 and 80, and the cap bottom engaging portion 74 is engaged with the distal end side of the raising base accommodating space 24 that functions as the distal-end-side engaging portion 20a.

Thus, the cover 30 and the cleaning cap 61 can be positioned in a predetermined state of the distal end component portion 20, and the cover 30 and the cleaning cap 61 are also prevented from moving in the distal end direction along the insertion-portion longitudinal axis a2 and from falling off the distal end component portion 20. In addition, the cleaning cap 61 can be restricted from turning around the insertion-portion longitudinal axis a2.

Therefore, the cleaning cap 61 can be prevented from moving by a jetting pressure of the cleaning liquid when the cleaning liquid is jetted from the ejection ports M1, M2, M3, and M4 to the distal end component portion 20, and can reliably perform cleaning.

In a plurality types of endoscopes having different types having different diameters or lengths in the distal end component portion of the endoscope, the body engaging portion having both a function of positioning and a function of preventing from moving to the distal end side and falling off is appropriately set for each endoscope. Then, the position and shape of the cover-side engaging portion 34 of the cover 30 and the position and shape of the cap-side engaging portion 75 of the cleaning cap 61 are set for each endoscope according to the type of each endoscope.

The present invention is not limited to the embodiment described above, and various modifications can be made without departing from the scope of the invention.

What is claimed is:

1. A cleaning tool comprising:
   a cleaning cap configured to be attachable to and detachable from a distal end component portion provided on a distal end side of an insertion portion in an insertion instrument and covered by a tubular cover when the insertion instrument is used, attachment and detachment of the cleaning cap to and from the distal end component portion being performed in a state where the cover is removed from the distal end component portion;

a cap-side engaging portion provided on the cleaning cap and configured to be engaged with a distal end component portion-side engaging portion provided on an outer peripheral surface, at least a part of which is covered by the cover, of the distal end component portion;

a first opening provided to the cleaning cap, the first opening being formed on a first surface that faces the distal end component portion in a state where the cleaning cap is mounted to the distal end component portion; and a first conduit configured to communicate with an inner surface of the cleaning cap through the first opening.

2. The cleaning tool according to claim 1, wherein the cap-side engaging portion has a same shape as a shape of a cover-side engaging portion provided on the cover and engaging with the distal end component portion-side engaging portion when the cover is mounted on the distal end component portion.

3. The cleaning tool according to claim 1, wherein the distal end component portion-side engaging portion, and the cover-side engaging portion and the cap-side engaging portion that engage with the distal end component portion-side engaging portion differ in shape depending on a type of the insertion instrument that does not presuppose being assembled with the same cover or the same cap.

4. The cleaning tool according to claim 1, wherein the cleaning cap includes a cap bottom engaging portion on a bottom surface side of a tubular portion formed when being mounted on the distal end component portion.

5. The cleaning tool according to claim 4, wherein the cap bottom engaging portion engages with an engaging portion provided on a distal end side of the distal end component portion.

6. The cleaning tool according to claim 4, wherein the cap bottom engaging portion engages with an engaging portion provided on a distal end side of the distal end component portion to restrict a turning position around an axis.

7. The cleaning tool according to claim 1, wherein the cap-side engaging portion engages with the distal end component portion-side engaging portion provided on a proximal end side of the distal end component portion.

8. The cleaning tool according to claim 7, wherein the cap-side engaging portion engages with the distal end component portion-side engaging portion to prevent the cleaning cap from moving in a longitudinal axis direction of the distal end component portion and falling off the distal end component portion.

9. The cleaning tool according to claim 1, further comprising a tube connected to the first conduit.

10. The cleaning tool for insertion instrument according to claim 1, wherein the cleaning cap further includes a second opening provided at a position different from a position of the first opening, and the cleaning tool for insertion instrument further comprises a second conduit that communicates with the second opening.

11. The cleaning tool according to claim 10, further comprising a branching portion comprising an inlet and first and second outlets, the first and second outlets are respectively connected to the first and second conduits.

12. The cleaning tool according to claim 1, wherein the cleaning cap is formed in a shape of a tube, and the first surface is the inner surface of the cleaning cap.

13. The cleaning tool according to claim 12, wherein the cleaning cap includes a first cap member and a second cap member movable relative to each other between an open position and a closed position where the cleaning cap is mounted to the distal end component portion, and each of the first cap member and the second cap member has an arc-shaped cross section.

\* \* \* \* \*